US011247949B2

(12) United States Patent
Dube

(10) Patent No.: US 11,247,949 B2
(45) Date of Patent: Feb. 15, 2022

(54) SYSTEM AND METHOD FOR CONVERSION OF METHANE INTO HYDROCARBON FUELS

(71) Applicant: Roger R. Dube, Dube, NY (US)

(72) Inventor: Roger R. Dube, Dube, NY (US)

(73) Assignee: GTL Systems, Inc., Boca Raton, FL (US)

( * ) Notice: Subject to any disclaimer, the term of this patent is extended or adjusted under 35 U.S.C. 154(b) by 0 days.

(21) Appl. No.: 16/367,169

(22) Filed: Mar. 27, 2019

(65) Prior Publication Data

US 2020/0308084 A1 Oct. 1, 2020

(51) Int. Cl.
| | |
|---|---|
| C07C 2/76 | (2006.01) |
| C07C 29/48 | (2006.01) |
| C07C 2/80 | (2006.01) |
| C10L 1/04 | (2006.01) |
| B01J 19/12 | (2006.01) |
| C10L 1/02 | (2006.01) |
| C10G 50/00 | (2006.01) |

(52) U.S. Cl.
CPC .............. *C07C 2/76* (2013.01); *B01J 19/123* (2013.01); *C07C 2/80* (2013.01); *C07C 29/48* (2013.01); *C10G 50/00* (2013.01); *C10L 1/02* (2013.01); *C10L 1/04* (2013.01); *B01J 2219/0875* (2013.01); *B01J 2219/1203* (2013.01); *C10G 2300/1025* (2013.01)

(58) Field of Classification Search
CPC combination set(s) only.
See application file for complete search history.

(56) References Cited

U.S. PATENT DOCUMENTS

| | | | | |
|---|---|---|---|---|
| 2005/0288541 | A1* | 12/2005 | Sherwood | C07C 2/76 585/324 |
| 2014/0367245 | A1* | 12/2014 | Dube | B01J 19/127 204/157.61 |
| 2017/0226431 | A1 | 8/2017 | Schechner | |
| 2018/0221847 | A1 | 8/2018 | Wong | |

FOREIGN PATENT DOCUMENTS

RU 2265585 C2 12/2005

OTHER PUBLICATIONS

"International Preliminary Report on Patentability for PCT Patent Application No. PCT/US2020/025225", dated Sep. 28, 2021, 5 Pages.

(Continued)

*Primary Examiner* — Medhanit W Bahta
(74) *Attorney, Agent, or Firm* — Medley, Behrens & Lewis, LLC

(57) ABSTRACT

An invention is provided for conversion of methane into hydrocarbon fuels is disclosed. The invention includes providing methane to an illumination chamber, and illuminating the methane with substantially narrow bandwidth photons of a predefined wavelength. The photons are provided from a substantially uncollimated light source producing photon intensities less than 10 Watt/m$^2$. As a result, the methane is placed in an excited state that results in the molecules of the methane reacting more readily with other molecules to form a final product.

19 Claims, 6 Drawing Sheets

(56) References Cited

OTHER PUBLICATIONS

"International Search Report for PCT Patent Application No. PCT/US2020/025225", dated Jul. 16, 2020, 2 Pages.
"Written Opinion of the International Searching Authority for PCT Patent Application No. PCT/US2020/025225", dated Jul. 16, 2020, 4 Pages.
Derk, et al., "Methane Conversion to Higher Hydrocarbons by UV Irradiation", In Industrial and Engineering Chemistry Research, vol. 47, No. 17, 2008, pp. 6568-6572.

* cited by examiner

SYSTEM AND METHOD FOR CONVERSION OF METHANE INTO HYDROCARBON FUELS

BACKGROUND OF THE INVENTION

Methane gas is a plentiful source of fuel, but as a greenhouse gas it presents issues in terms of global warming. It further offers a challenge in that it is a gas over a wide range of temperatures and cannot be easily converted to liquid for ease of transport to markets. "Gas to Liquids" (GTL) is a term used to describe a variety of processes that convert an input gas (for example, methane) to a longer chain hydrocarbon (ideally, a liquid). The vast majority of GTL processes in use and under development today employ heat and physical catalysts. One such example is the Fischer-Tropsch (F-T) process, named after the two inventors of the process. The F-T process burns some of the source gas (natural gas, consisting primarily of methane) to heat up a chamber of natural gas, which is then allowed to come into contact with a physical catalyst. The rapid movements of the heated molecules increase the likelihood that they will encounter the catalyst. On the surface of the catalyst, the molecules have a lower activation potential—that is, the barrier to a reaction (such as the combining of two methane molecules) is reduced, and longer chain hydrocarbons are created at a much higher rate than would occur otherwise.

One drawback to this conventional approach to producing longer chain hydrocarbons is that the process is very inefficient. Large amounts of heat must be produced to achieve the throughputs desired. A second drawback of this approach is that the catalyst "fatigues," where oxidation and the gradual accumulation of impurities reduces its efficiency over time. The catalyst must be replaced or reconditioned, and this is both an expensive and time-consuming process that incurs great expense to the user.

A third drawback of the F-T process is that a reasonable return on investment can only be achieved for very large F-T facilities. This precludes building a transportable or small system that can be taken to remote sources of gas. Approximately one-third of all natural gas is said to be "stranded"—that is, it is located at a place where it cannot be accessed at a reasonable cost. Finally, the F-T process is not species-specific. That is, it is not possible to tune the process to produce a single final long chain hydrocarbon. By its very nature, it produces a wide distribution of hydrocarbons, thereby requiring the subsequent separation of these products using fractionation, another large, expensive process.

In response, additional approaches have been proposed. One approach to enabling chemical reactions is through the introduction of photons of sufficient energy to break molecular bonds. Early work by Morrey (U.S. Pat. No. 4,124,466, 1978) introduced lasers to enhance chemical reactions. At the time of that patent, lasers were the only source of ultra-high intensity beams of collimated photons, but they suffered from producing only long wavelength (low energy) photons. Morrey introduced a non-linear crystal which produced a doubling of the photon frequency (thereby producing a beam of half the wavelength). These frequency doubled photons had sufficient energy to break the chemical bonds, but the technique suffered from extremely low frequency doubling efficiencies.

An alternative approach was described by Geiger, U.S. Pat. No. 5,328,575, issued in 1994. Geiger speaks to the reaction of at least 2 hydrocarbons to produce a third and higher hydrocarbon species, and cites conversions such as methane to ethane and higher hydrocarbons as an example result of the process. Geiger's system uses a chamber into which the first hydrocarbon is injected through a high temperature nozzle, and is surrounded by an array of optical parametric oscillators/lasers (OPO) which provide high intensities of short wavelength photons. This approach suffers from the use of a costly and delicate instrument that increases frequency doubling, which was required at the time of the patent. There is a need to make a system that is more practical.

Another approach is described in a patent publication by Gondal, US Patent Publication 2005/0045467, in which the inventor discloses the use of high intensity Nd:Yag lasers to photo-dissociate molecules of methane in order to break the C—H bonds to enable subsequent reactions that form higher hydrocarbons, such as ethane, ethylene, propane, propylene and isobutane.

There are three basic problems with this approach. First, lasers are expensive and are not well suited to volume photochemistry. By their nature, as illustrated in FIG. 1, lasers produce a small (millimeter) diameter beam of high intensity collimated light. Gondal describes the use of an Nd:YAG laser—this is a high power, water cooled laser that is not practical for the field on its own merit. In order to be excited by a photon from a laser source, a target molecule must pass through the laser beam. Gondal reveals a method in his disclosure where he further increases the intensity of the photon beam by focusing the already small beam to as fine a point as possible. Since the beam is small (usually on the order of a millimeter), a very small fraction of a volume of molecules is likely to pass through the small beam at any time. This leads to long exposure times (Gondal cites exposure times of 20-60 minutes) in order to get any appreciable reaction. Second, Gondal's disclosure only addresses the photochemistry of methane alone without additional reactants, and its subsequent byproducts of high hydrocarbons using only carbon and hydrogen. This approach does not address more complex and commercially valuable products such as ethanol which are obtained through the use of multiple molecular species. Third, the laser and its power supply together weigh in excess of 400 pounds and they require cooling water flowing at the rate of 4 liters per minute. This limits the portability and use of the technology in remote locations.

Hence, there is a need to convert methane gas and other hydrocarbons to longer chain hydrocarbons that can be transported in liquid form, if this conversion can be accomplished economically. Ideally, this conversion should be accomplished at the site of the natural gas to avoid a need for costly pipelines. Thus, there is a need to develop a low cost, light weight, efficient process to convert methane gas to a liquid fuel such as, for example, ethanol. Ideally the system should be small and portable and require minimum cooling for the light source.

SUMMARY OF THE INVENTION

Broadly speaking, embodiments of the present invention provide a low intensity optical photochemical reactor process that employs small, low cost, low intensity UV-c light sources to provide uncollimated photons with sufficiently short wavelength (i.e. high energy) to break molecular bonds such as, for example, the C—H bond of methane and O—H bond of water. In one embodiment, a method for conversion of methane into hydrocarbon fuels is disclosed. The method includes providing methane to an illumination chamber and illuminating the methane with substantially narrow bandwidth photons of a predefined wavelength. The photons are provided from a substantially uncollimated light source producing photon intensities less than 10 Watt/m2. As a result, the methane is placed in an excited state that results in the molecules of the methane reacting more readily with other molecules to form a final product. For example, the other molecules can be hydrocarbon molecules and the final product can be propane. In another example, water vapor can be provided to a reaction chamber with the methane and the final product can be ethanol. The reaction chamber can be a volume in which the reaction occurs, and may or may not be the same volume in which the illumination and excitation occurs. As such, the reaction chamber and the illumination chamber are a conceptual identification of volumes and not necessarily separate physical volumes. The wavelength generally is in the range of about 150 nm to 200 nm, and often in the range of about 170 nm to 190 nm. The low intensity light source can produce photon intensities in the range of about 0.25 Watt/$m^2$ to 4 Watt/$m^2$, such as from an ultraviolet C (UVC) light.

A further method for conversion of methane into hydrocarbon fuels is disclosed in an additional embodiment of the present invention. As above, the method includes providing a first chemical to a first illumination chamber. In addition, a second chemical is provided to a second illumination chamber. The first chemical is illuminated with substantially narrow bandwidth photons of a predefined wavelength from a substantially uncollimated light source producing photon intensities less than 10 Watt/$m^2$. As a result, the first chemical is placed in an excited state that results in the molecules of the first chemical being more likely to react with other molecules. Similarly, the second chemical is illuminated with substantially narrow bandwidth photons of a predefined wavelength from a substantially uncollimated light source producing photon intensities less than 10 Watt/$m^2$. As above, this causes the molecules of a second chemical being placed in an excited state that results in the molecules of the second chemical being more likely to react with other molecules. Next, the first chemical and the second chemical, both in the excited state, are provided to a reaction chamber (which may or may not be the same as the illumination chamber), wherein molecules of the first chemical bond with molecules from the second chemical in a predefined manner to form a final product. The method can further include providing unreacted molecules of the first chemical and/or the second chemical back to the first, and/or second respectively, illumination chamber. In this case, additional illumination and reaction of the unreacted first chemical and second chemical can be performed to form additional final product. The final product can then be provided to a local storage. Optionally, the first chemical and/or second chemical can be compressed prior to illumination.

A system for conversion of methane into hydrocarbon fuels is disclosed in a further embodiment of the present invention. The system includes an illumination chamber and a substantially uncollimated light source producing photon intensities less than 10 Watt/$m^2$ and having a predefined substantially narrow bandwidth wavelength. The uncollimated light source provides illumination to a chemical within the illumination chamber causing the molecules of the chemical to enter an excited state. The term "excited state" in this disclosure includes either a molecule whose electrons have been moved to higher orbitals (which have lower activation barriers for reaction with other molecules) OR a molecule whose chemical bonds (formed by a shared electron) have been broken by the photoionization of the electron from its orbital OR a molecule with electrons missing from certain orbitals (these molecules are usually referred to as ions). In practice, the illumination and reaction chambers may optionally be the same chamber or different chambers, depending on the lifetimes of the excited states of the molecules. In operation, molecules of the chemical in the excited state are provided to the reaction chamber and bond with other molecules to form a final product. In this system the chemical typically is methane and the final product can be propane, ethanol, or other hydrocarbon fuel. As above, the wavelength can be in the range of about 170 nm to 190 nm and the uncollimated light source can produce photon intensities in the range of about 0.25 Watt/$m^2$ to 4 Watt/$m^2$.

Advantageously, embodiments of the present invention do not require the use of a laser or other collimated sources of photons because the energy of the photon is all that matters, not its coherence with other photons nor its existence in a tightly collimated beam of light. Further, embodiments of the present invention do not require water cooling of the light source. Moreover, the light source of the embodiments of the present invention, particular when used with appropriately positioned reflecting surfaces, produce photons that bounce back and forth many times through the illumination chamber, thereby increasing the likelihood of absorption and its consequential reduction of the activation barrier.

For example, using the above described operations and systems, embodiments of the present invention can achieve efficient conversion of methane and water to ethanol using light of intensities on the order of 1 W/$m^2$ during exposures on the order of 60 seconds, as opposed to the intensities described above in excess of $1 \times 10^{10}$ W/$m^2$ and exposures of 20-60 minutes.

BRIEF DESCRIPTION OF THE DRAWINGS

The invention, together with further advantages thereof, may best be understood by reference to the following description taken in conjunction with the accompanying drawings in which.

DETAILED DESCRIPTION OF THE EMBODIMENTS

Embodiments of the present invention relate to a system and method for enhanced chemical reactions via optical excitation of molecules. Excitation in the present disclosure refers to moving electrons from one orbital up to a higher level orbital, also called an excited state, or the complete ejection of or breaking a bond between two molecules by causing the photoionization of a binding electron by incoming high energy photons. Embodiments of the present invention provide this excitation via low intensity, uncollimated monochromatic or substantially narrow bandwidth light at a particular wavelength.

In this manner, embodiments of the present invention are capable of converting methane gas and other hydrocarbons to longer chain hydrocarbons economically, allowing the longer chain hydrocarbons to be transported in liquid form. This conversion can be accomplished at the site of the natural gas, thereby avoiding a need for costly pipelines. Thus, embodiments of the present invention provide a low cost, light weight, efficient process to convert methane gas to a liquid fuel such as, for example, ethanol. The system is small and portable and, because of the low intensity, requires minimum cooling for the light source.

More specifically, embodiments of the present invention use low intensity, uncollimated and substantially narrow bandwidth light at a particular wavelength to create an excited state of a particular molecule that results in the molecule being more reactive for a reasonable amount of time, either through excitation of an electron to a higher orbital or through photoionization (breaking) of a specific bond. The molecules are thus illuminated to achieve enhanced reactions.

In this excited state, the molecules are more likely to react with other molecules. Random molecular motion of these molecules causes them to collide with other similarly excited molecules, and in some cases these collisions cause a chemical bonding. The specific wavelength of light that excites a molecule to such a state is based on the properties and atomic structure of the particular molecule, and can be different for different chemical reactions. It is possible that there might be intermediate states between the original molecule and the final reaction product. Such intermediate states may or may not be important to the overall process of optical conversion without detracting from the present invention. As such, embodiments of the present invention provide a system and method for enabling the rapid reaction of a chemical species with itself or other chemical species using carefully chosen wavelengths of light to enhance the reaction rate.

Figure 2:
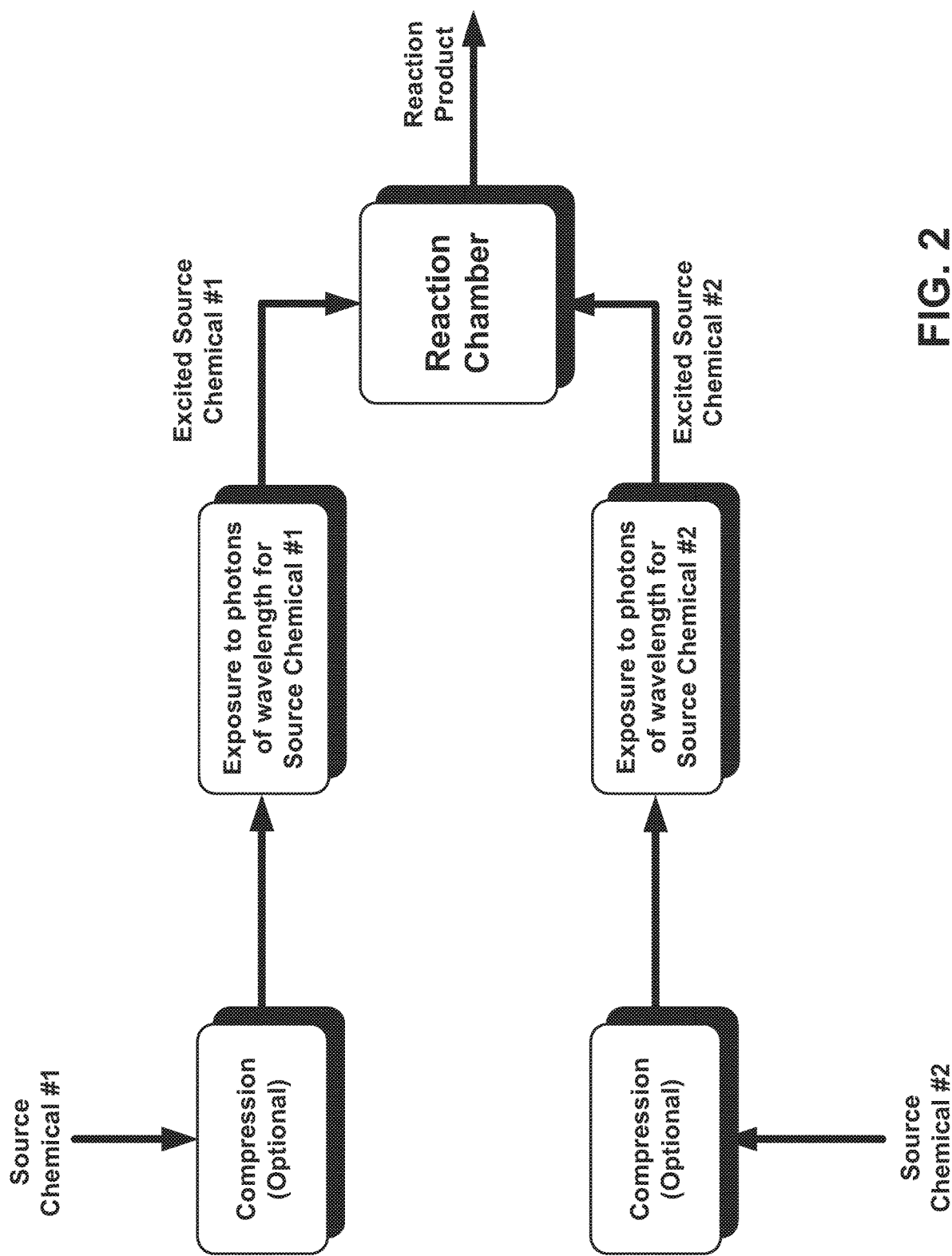
FIG. 2 illustrates a system for converting methane into hydrocarbon fuels, in accordance with an embodiment of the present invention.

For example, FIG. 2 illustrates a system for converting methane into hydrocarbon fuels, in accordance with an embodiment of the present invention. As illustrated in FIG. 2, two source chemicals that are to be combined are provided to the system. These chemicals can be in any form, such as a gas or liquid, and can be different from one another. Although FIG. 2 shows an example of two molecular species and illumination chambers, it should be noted that a third illumination chamber and a third molecular species can be illuminated with its own wavelength and then combined with either of other the two molecular species (i.e., chemicals) in the reaction. That is, the number of molecular species and illumination chambers are not limited to one or two, and include any number of such species and chambers. Additional embodiments can for example illuminate the third molecular species and allow it to react with the product of the other two molecular species reaction. This can continue to be daisy chained to reach a specific goal.

Optionally, one or both chemicals can be compressed, in the same or different physical volumes, for enhanced illumination and reaction, depending on the exact chemicals utilized and the needs of the particular system. After the optional compression, the chemicals are provided to an illumination chamber where each chemical is illuminated by its own private excitation wavelength that results in the desired excited state. In general, the desired excited state results in the enhanced ability of the molecules of the particular chemical to bond more readily in a desired manner with the molecules of the other chemical provided to the system.

In the example of FIG. 2, source chemical 1 is illuminated by light, generally monochromatic light at a particular wavelength 1. Simultaneously, source chemical 2 is illuminated by monochromatic light of wavelength 2. In one embodiment, wavelength 1 selectively excites chemical 1, while wavelength 2 selectively excites chemical 2.

As mentioned above, embodiments of the present invention illuminate the source chemicals using a substantially narrow bandwidth low intensity light source having a predefined wavelength disposed within the illumination chamber. The light source produces substantially uncollimated light having photon intensities less than 10 Watt/m$^2$.

Figure 1:
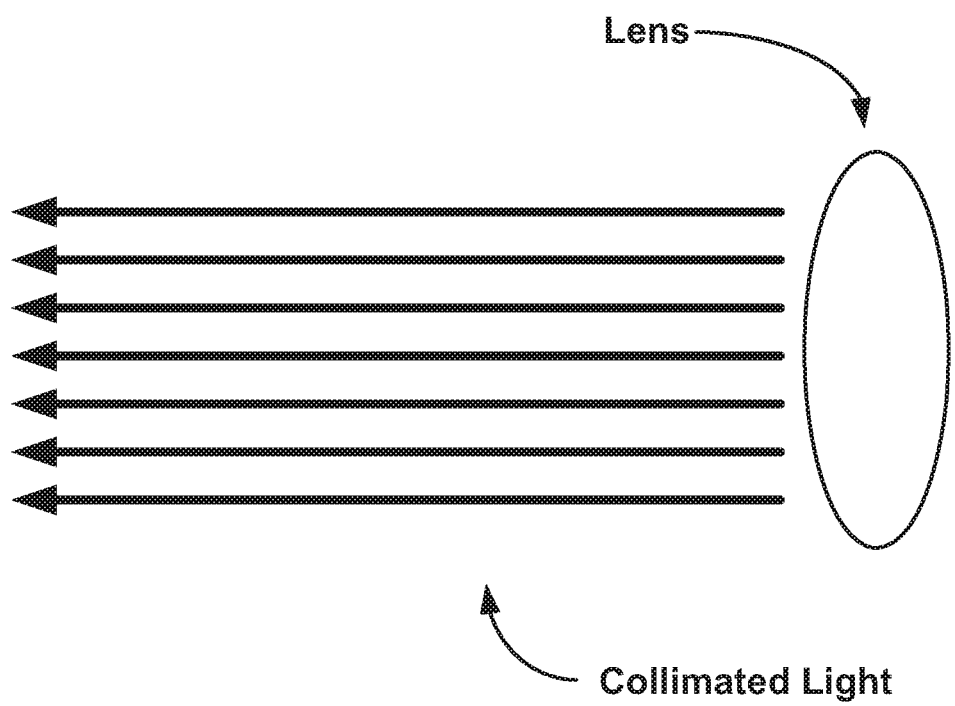
FIG. 1 is an exemplary prior art collimated light source.
Figure 3:
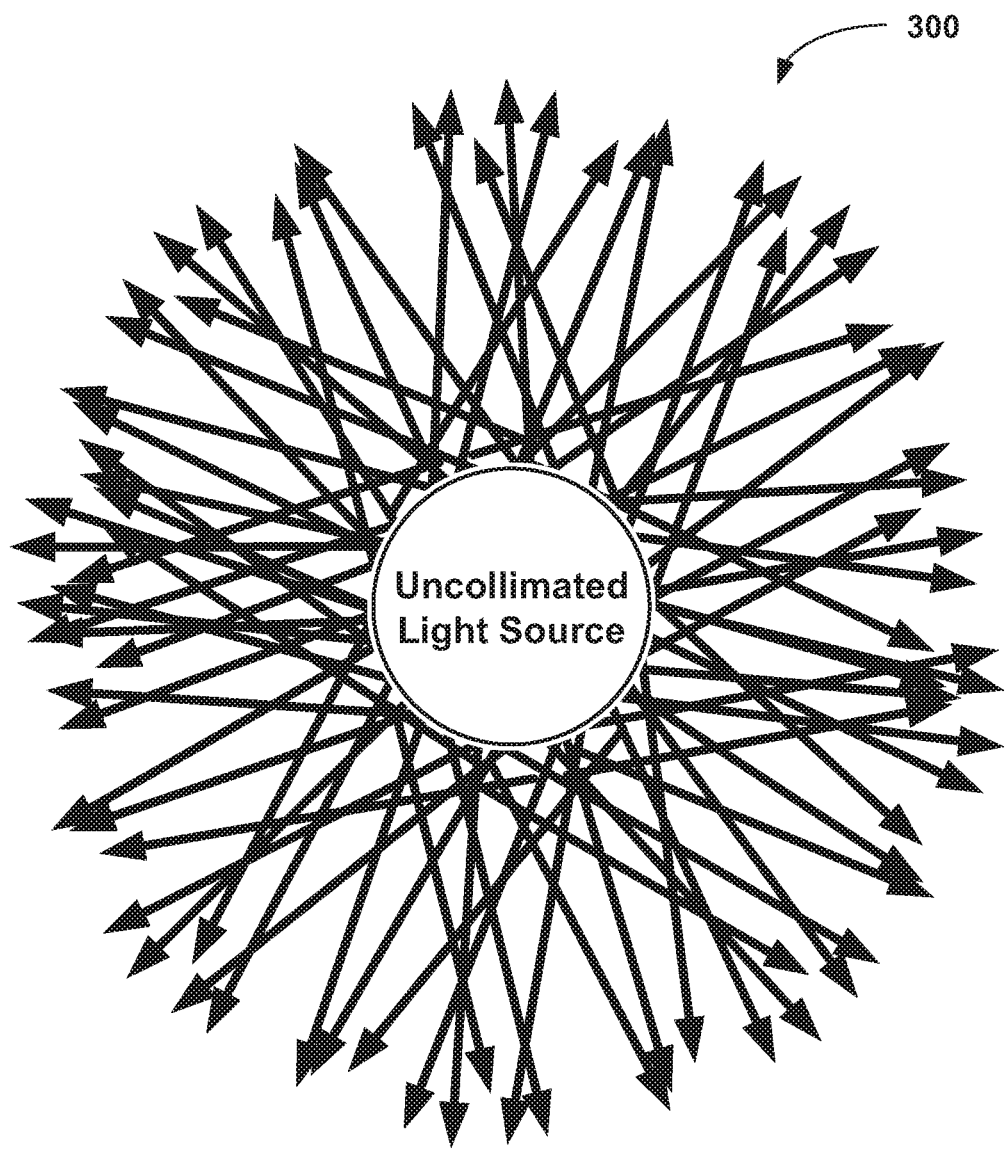
FIG. 3 is an illustration showing substantially uncollimated light, in accordance with an embodiment of the present invention.

FIG. 3 is an illustration showing substantially uncollimated light 300, in accordance with an embodiment of the present invention. Unlike a laser, which produces highly collimated light as illustrated in prior art FIG. 1, the light source of the embodiments of the present invention emits incoherent and uncollimated light 300. The photons diverge immediately upon exiting the emitting surface of the light source, bathing the entire area of the illumination chamber with the light. Advantageously, even though these photons are not confined to a very small area as they are in laser beams utilized in the prior art, these photons have the same energy as their laser counterparts that are of the same wavelength.

As a result, embodiments of the present invention do not require the use of a laser or other collimated sources of photons because the energy of the photon is all that matters, not its coherence with other photons nor its existence in a tightly collimated beam of light. Moreover, the light source of the embodiments of the present invention, particular when used with appropriately positioned reflecting surfaces, produce photons that bounce back and forth many times through the illumination chamber, thereby increasing the likelihood of absorption and its consequential reduction of the activation barrier. In one embodiment, the uncollimated light source is a UV or deep UV light source that produce photons having sufficient energy to impact the activation energy.

As mentioned previously, embodiments of the present invention utilize small, low cost, low intensity UV-c light sources to provide photons with sufficiently short wavelength (i.e. high energy) to break bonds such as the C—H bond of methane and the O—H bond of water. As will be described in greater detail subsequently, embodiments of the present invention can convert methane and water to ethanol using light of intensities on the order of 1 W/m$^2$ during exposures on the order of 60 seconds, as opposed to the intensities described in the prior art what are in excess of 1×10$^{10}$ W/m$^2$ with exposures of 20-60 minutes. Moreover, unlike the prior art, embodiments of the present invention do not require water cooling of the light source.

Referring back to FIG. 2, the excited species of chemical 1 and chemical 2 then are allowed to mix with one another, such that the molecules of source chemical 1 bond with the molecules of source chemical 2 in a desired manner. This reaction chamber may be coincident with the two illumination chambers, or may be a separate, subsequent chamber, depending on the lifetimes of the excited states and the flow rate of the species. Upon colliding, some fraction of the excited source chemicals is provided to a reaction chamber where the molecules of the excited source chemicals bond in the desired manner to form the reaction product.

In one embodiment, low intensity (for example, 1 W/m$^2$) ultraviolet photons are used to excite a mixture of methane and steam (water vapor) to produce a different molecular species, such as propane, ethanol or methanol, at light levels about 10$^{10}$ times lower than those used in the prior. In particular, one embodiment employs an uncollimated light source at the center of the illumination chamber having an intensity of between 0.25 Watt/m$^2$ and 4 Watt/m$^2$ of UV-c light with photons of wavelength between 170 and 190 nanometers. The illumination chamber in this embodiment includes a mixture of steam and methane gas at an average temperature between 70 and 100 degrees centigrade. In this example embodiment, the photons are allowed to be excited in the chamber for between 30 seconds and 60 seconds, thereby comprising an exposure time of 30-60 seconds. In contrast, prior art disclosures cite photon intensities of about 1×10$^{10}$ W/m$^2$ for exposure times between 30 and 60 minutes. Moreover, in this particular exemplary embodiment of the present invention, the reaction chamber and the illumination chamber are one and the same.

The disclosed embodiment produces molecular conversion efficiencies well in excess of 1%, in some cases reaching 40%. Conversion efficiencies of this level have not been cited in any prior art with systems operating at these low intensities, nor have they provided a means to produce these efficiencies on timescales of a minute, as opposed to their reported 30-60 minute timescales.

For example, methane gas (CH$_4$) can be excited by UV-c photons in an illumination chamber, and water vapor (H$_2$O) can be excited by the proper wavelength photons in the same or a different chamber. The two excited molecular volumes are brought together (if they were separate) to react, producing, for example, ethanol or propane plus hydrogen byproducts.

It should be apparent to one trained in the art after a careful reading of the present disclosure that the illumination chamber of one reactant can be coexistent with the illumination chamber of a second molecular species so that the two excited molecular species have a minimal travel time and maximum likelihood of collision with the complementary excited molecular species. In addition, embodiments of the present invention can use catalysts at one or more steps, should that prove to be advantageous. Such details of configurations should be understood by those trained in the art to be within the realm of this disclosure.

Embodiments of the present invention can be implemented as modules that are subsequently chained in sequence to create a system that converts a source gas (such as natural gas) to a target longer chain hydrocarbon (such as butane, gasoline, or diesel fuel). The present invention describes a system that achieves this goal through the use of carefully selected light sources and a supporting excitation/reaction system that allows the extraction of a final reaction product from the system right on site. Moreover, embodiments of the present invention can be applied to reactants in a liquid state, as well as a gas state.

Figure 4:
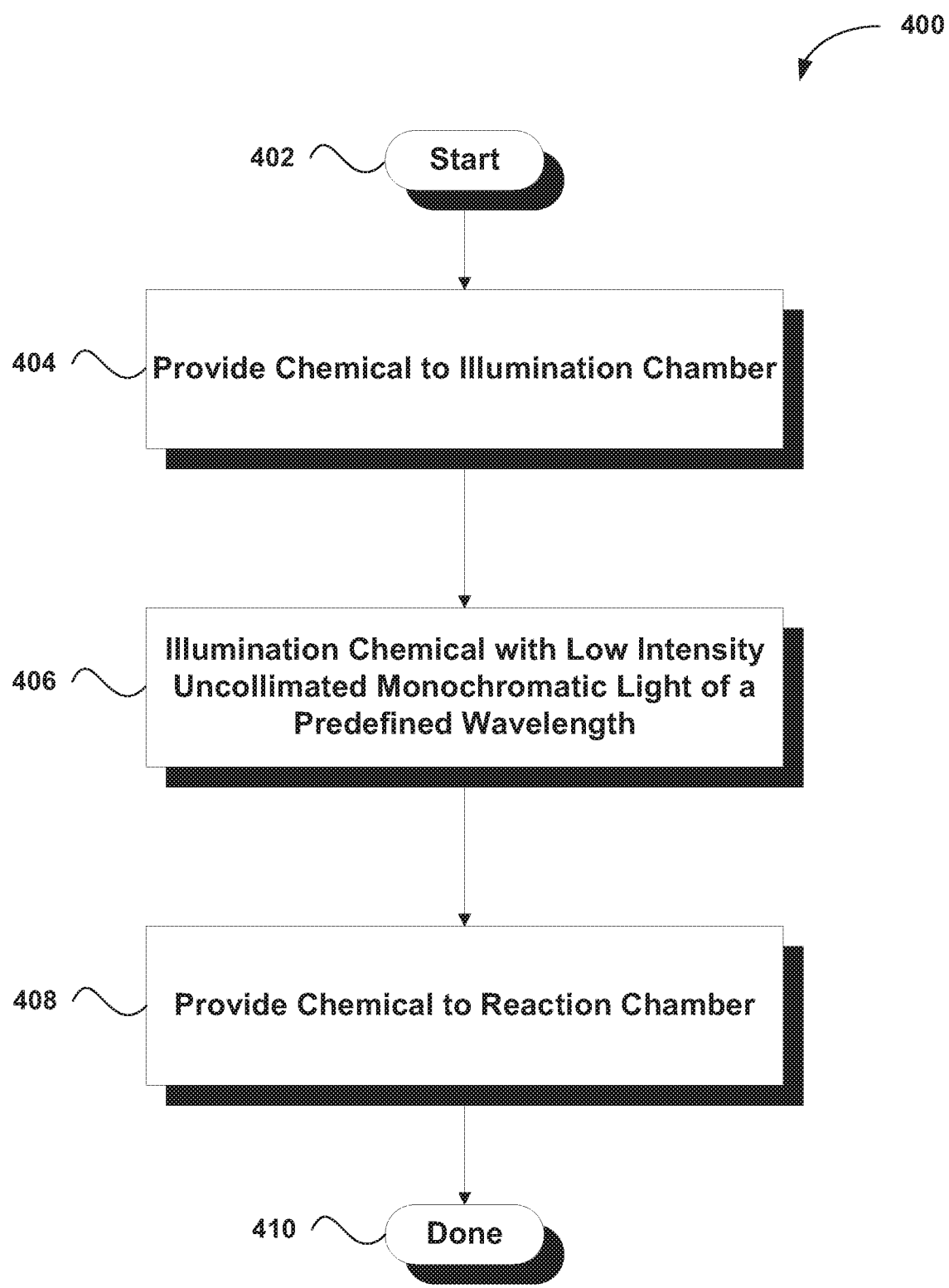
FIG. 4 is a flowchart showing a method for optical excitation of a chemical species for enhanced chemical reaction, in accordance with an embodiment of the present invention.

FIG. 4 is a flowchart showing a method 400 for optical excitation of a chemical species for enhanced chemical reaction, in accordance with an embodiment of the present invention. In an initial operation 402, preprocess operations are performed. Preprocess operations can include, for example, selecting a wavelength for the monochromatic light in the illumination chamber, selecting a chemical to excite, and further preprocess operations that will be apparent to those skilled in the art with hindsight provided after a careful examination of the present disclosure.

In operation 404, a chemical is provided to an illumination chamber. The chemical can be in any form, such as a gas or liquid, and can be optionally compressed for enhanced illumination and reaction, depending on the exact chemical utilized and the needs of the particular system.

The chemical then is illuminated with an uncollimated and substantially narrow bandwidth photons of a predefined wavelength, in operation 406. Each of the sources of uncollimated photons has an intensity less than 10 Watt/m$^2$ and typically between 0.25 Watt/m$^2$ and 4 Watt/m$^2$. As noted above, the predefined wavelength is selected such that illumination by the selected wavelength results in the desired excited state of the chemical molecules through orbital excitation or selective breaking of molecular bonds. For example, noted previously, methane gas can be illuminated by monochromatic light at a wavelength of between 170 and 190 nanometers to cause the methane gas to react to form longer chain hydrocarbons. As a result of the illumination, the chemical is placed in an excited state, wherein the excited state results in the molecules of the chemical reacting more rapidly with other molecules to form a final product. That is, the desired excited state results in the molecules of the particular chemical to bond in a desired manner with the molecules of the same or another chemical provided to the system.

The chemical in the excited state is then provided to a reaction chamber where the molecules of the chemical bond with other molecules in a predefined manner. The reaction chamber can be coincident with the illumination chamber, or can be a separate, subsequent chamber, depending on the lifetimes of the excited states and the flow rate of the species. The molecules of the excited source chemical bond in the desired manner to form the reaction product.

Post process operations then are performed in operation 410. Post process operations can include, for example, returning an unreacted portion of the chemical back to the illumination chamber for further processing, condensation of a gaseous state of a final molecular species to a liquid state, storing the reacted portion of the chemical (i.e., the portion wherein the molecules bonded in the desired manner) to a local storage, and other post process operations that will be apparent to those skilled in the art with the hindsight afforded after a careful reading of the present disclosure. For example, a post process operation might include the purification of a fuel through distillation or fractionation. In addition to combining multiple chemicals, embodiments of the present invention can be utilized for unification of a single chemical to produce longer molecular chains that are more attractive than the original source molecule.

Figure 5:
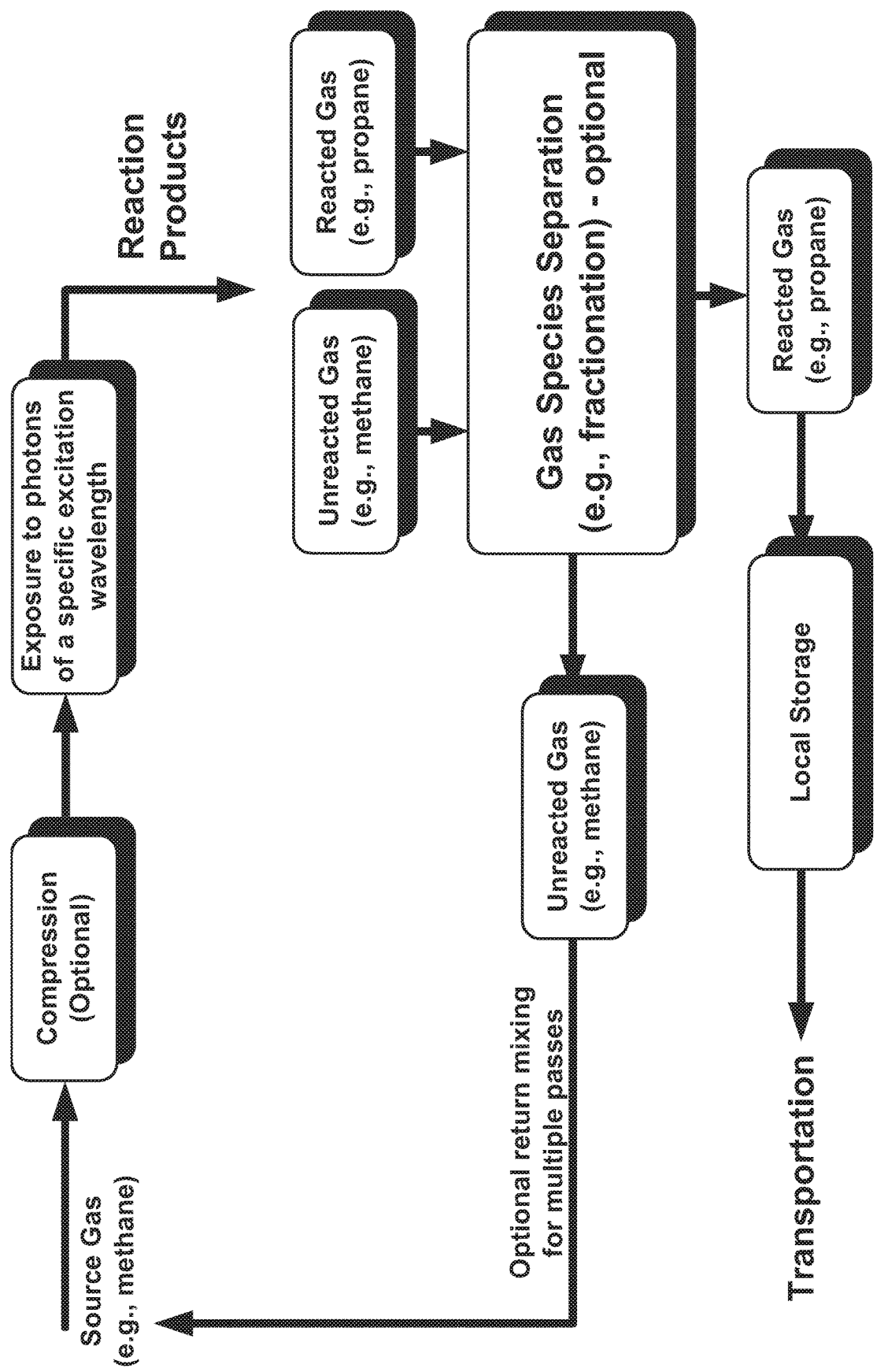
FIG. 5 illustrates a system for converting methane into hydrocarbon fuels, in accordance with an embodiment of the present invention.

FIG. 5 illustrates a system for converting methane into hydrocarbon fuels, in accordance with an embodiment of the present invention. As described above, embodiments of the present invention disclose a low intensity optical photochemical reactor process that employs small, low cost, low intensity UV-c light sources to provide photons with sufficiently short wavelength (i.e. high energy) to break bonds such as the C—H bond of methane and the O—H bond of water. Embodiments of the present invention can achieve efficient conversion of methane and water to ethanol using light of intensities on the order of 1 W/m$^2$ during exposures on the order of 60 seconds, as opposed to the intensities described above in excess of 1×10$^{10}$ W/m$^2$ and exposures of 20-60 minutes. Our system did not require water cooling of the light source.

There are many possible configurations for causing an input stream of gas (in the specific instance of FIG. 5, the input gas is methane) to be exposed to excitation light of a specific wavelength, and then separating the results into streams of the desired end product (such as propane or ethanol) and unreacted gas. The end result can be sent on to a storage tank of some sort, and the unreacted gas can optionally be returned back to mix with the original input stream for an additional pass. This disclosure also presents a configuration in which a raw input stream is stored in a collection tank and later sent into an exposure station where the molecules are exposed to a specific wavelength of light. The result is a mixture of the desired end product and the source gas. These can be separated through standard means known to those skilled in the art, and the unreacted gas can then be returned to mix with the input stream for a second (or even third, fourth, etc.) pass.

Figure 6:
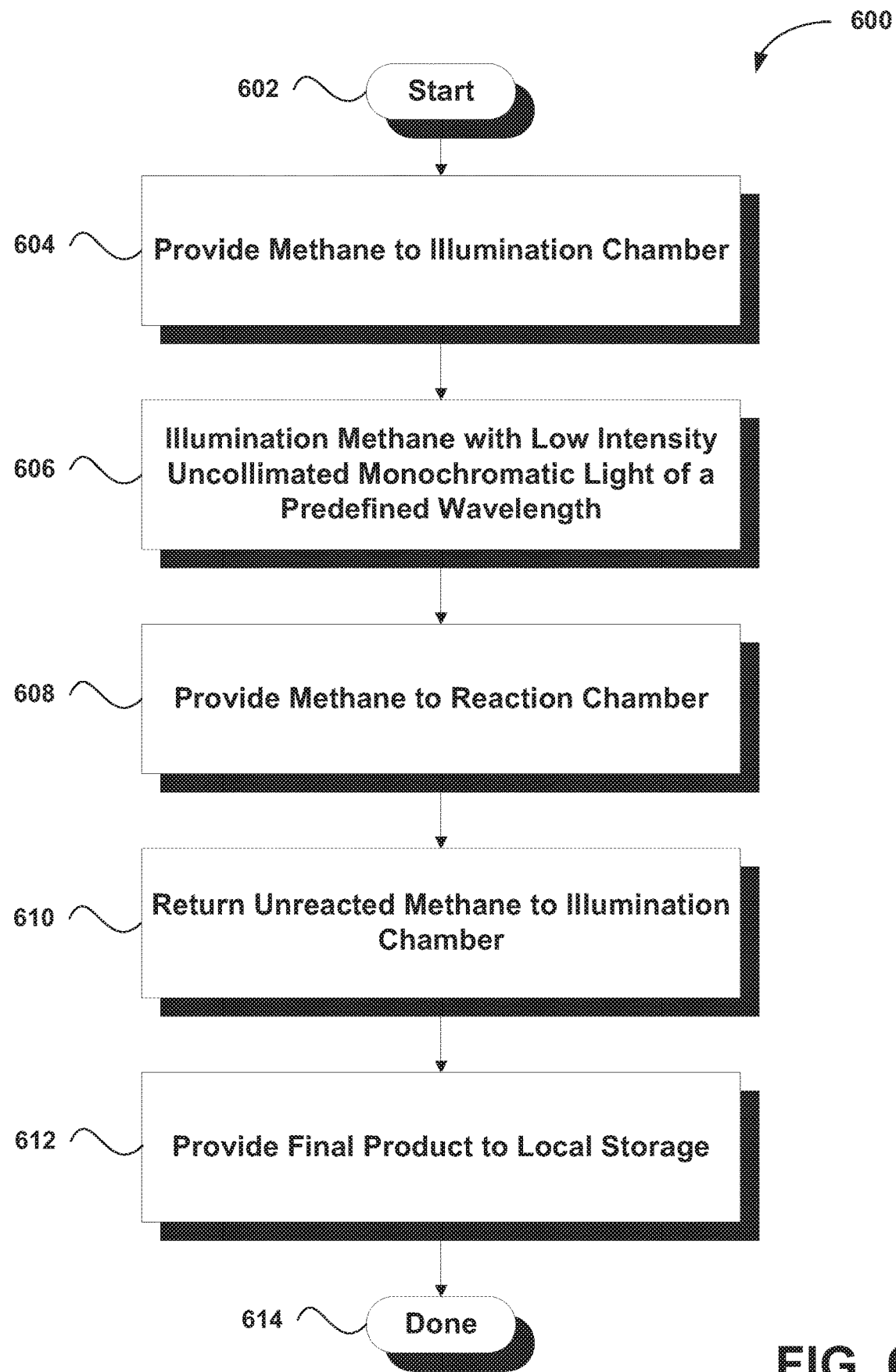
FIG. 6 is a flowchart showing a method for conversion of methane into hydrocarbon fuels, in accordance with an embodiment of the present invention.

FIG. 6 is a flowchart showing a method 600 for conversion of methane into hydrocarbon fuels, in accordance with an embodiment of the present invention. In an initial operation 602, preprocess operations are performed. Preprocess operations can include, for example, selecting a wavelength for the uncollimated, low intensity, monochromatic light in the illumination chamber (typically in the range of about 170 nm and 190 nm), determining whether to use compression prior to illumination, and further preprocess operations that will be apparent to those skilled in the art with hindsight provided after a careful examination of the present disclosure.

In operation 604, methane is provided to an illumination chamber. As above, the methane can be in any form, such as a gas or liquid, and can be optionally compressed for enhanced illumination and reaction, depending on the needs of the particular system.

The methane then is illuminated with a low intensity, substantially narrow bandwidth or monochromatic light of a predefined wavelength, in operation 606. As noted above, the predefined wavelength is selected such that illumination by the selected wavelength results in the desired excited state of the chemical molecules. As discussed previously, in one embodiment a low intensity (for example, 1 W/m2) ultraviolet photons are used to excite a mixture of methane and steam (water vapor) to produce a different molecular species, such as propane, ethanol or methanol, at light levels about $10^{10}$ times lower than those used in the prior art.

In this embodiment, an uncollimated light source is disposed at the center of the illumination chamber having an intensity of between 0.25 Watt/m$^2$ and 4 Watt/m$^2$ of UV-c light with photons of wavelength between 170 and 190 nanometers. The illumination chamber in this embodiment includes a mixture of steam and methane gas at an average temperature between 70 and 100 degrees centigrade. In this example embodiment, the photons are allowed to excited the chamber for between 30 seconds and 60 seconds, thereby comprising an exposure time of 30-60 seconds. In contrast, prior art disclosures cite photon intensities of about $1 \times 10^{10}$ W/m$^2$ for exposure times between 30 and 60 minutes.

However, it should be noted that it is also possible to place the light source outside the illumination chamber and use a mirror to reflect the majority of photons that would naturally be leaving the area back into the illumination chamber. In this embodiment, the light is outside the illumination chamber and thus is not susceptible to possible buildup of contaminants or other particles and oils from the chemicals on its emitting surface. In this aspect, only the inside of the illumination chamber may have to be cleaned occasionally. The material of the window into the chamber can be chosen carefully to allow the short wavelength photons to pass through into the chamber.

In operation 608, the methane in the excited state is then provided to a reaction chamber where the molecules bond with other molecules in a predefined manner. As noted above, the excited methane molecules react with and bond to other excited methane molecules, producing propane molecules.

In optional operation 610, the unreacted methane molecules are returned to the illumination chamber for further processing. In some embodiments some methane molecules will fail to react with other methane molecules. As a result, the two chemicals can remain in the reaction chamber after chemical reaction: 1) methane formed from unreacted methane molecules, and 2) propane formed from reacted methane molecules that have bonded to form propane molecules. Hence, in optional operation 610, the unreacted methane molecules can be optionally returned to the illumination chamber for further processing, depending on the needs of the particular system.

In operation 612, the propane molecules are provided to local storage. The end result can be sent on to a storage tank of some sort, and the unreacted gas can optionally be returned back to mix with the original input stream for an additional pass as noted in operation 610. In one embodiment the raw input stream is stored in a collection tank and later sent into an exposure station where the molecules are exposed to a specific wavelength of light. The result is a mixture of the desired end product and the source gas. These can be separated through standard means known to those skilled in the art, and the unreacted gas can then be returned to mix with the input stream for a second (or even third, fourth, etc.) pass.

Although the foregoing invention has been described in some detail for purposes of clarity of understanding, it will be apparent that certain changes and modifications may be practiced within the scope of the appended claims. Accordingly, the present embodiments are to be considered as illustrative and not restrictive, and the invention is not to be limited to the details given herein, but may be modified within the scope and equivalents of the appended claims.

What is claimed is:

1. A method for conversion of methane into hydrocarbon fuels, comprising:
providing methane to an illumination chamber, and
illuminating the methane with narrow bandwidth photons of a wavelength in the range of about 150 nm to 200 nm from an uncollimated ultraviolet light source producing photon intensities less than 10 Watt/m$^2$, wherein the methane is placed in an excited state, and wherein the excited state results in the molecules of the methane reacting more readily with other hydrocarbon molecules to form a final product of hydrocarbon fuel.

2. A method as recited in claim 1, wherein the other molecules are hydrocarbon molecules and the final product is propane.

3. A method as recited in claim 1, further comprising the operation of providing water vapor and the methane to a reaction chamber.

4. A method as recited in claim 3, wherein the final product is ethanol.

5. A method as recited in claim 1, wherein the wavelength is in the range of about 170 nm to 190 nm.

6. A method as recited in claim 1, wherein the light source produces photon intensities in the range of about 0.25 Watt/m$^2$ to 4 Watt/m$^2$.

7. A method as recited in claim 1, wherein the light source is an ultraviolet C (UVC) light.

8. The method of claim 1, wherein in the excited state, an electron of the methane is excited to a higher orbital than occupied by the electron prior to illumination of the methane.

9. The method of claim 1, wherein in the excited state the methane is photoionized.

10. The method of claim 1, wherein the methane is in a liquid state prior to illumination.

11. The method of claim 1, wherein water vapor is also present within the illumination chamber during illumination of the methane.

12. A method for conversion of methane into hydrocarbon fuels comprising:
   providing methane molecules to a first illumination chamber;
   providing water molecules to a second illumination chamber;
   illuminating the methane molecules with narrow bandwidth photons of a wavelength in the range of about 150 nm to 200 nm from an uncollimated ultraviolet light source producing photon intensities less than 10 Watt/m$^2$, wherein the methane molecules are placed in an excited state, and wherein the excited state results in the methane molecules being more likely than before excitation to react with other molecules of water;
   illuminating the water molecules with narrow bandwidth photons from an uncollimated ultraviolet light source producing photon intensities less than 10 Watt/m$^2$, wherein the water molecules are placed in an excited state, and wherein the excited state results in the water molecules being more likely than before excitation to react with other molecules of methane; and
   providing the methane molecules in the excited state and the water molecules in the excited state to a reaction chamber, wherein methane molecules bond with water molecules to form a final product of hydrocarbon fuel.

13. The method of claim 12, wherein the methane molecules and the water molecules are illuminated for a duration of between 30 and 60 seconds.

14. The method recited in claim 12, further comprising providing unreacted molecules of methane from the reaction chamber back to the first illumination chamber.

15. The method recited in claim 14, further comprising providing unreacted molecules of water from the reaction chamber back to the second illumination chamber.

16. The method recited in claim 15, further comprising performing additional illumination and reaction of the unreacted methane molecules and water molecules to form additional final product.

17. The method recited in claim 12, further comprising providing the final product to a local storage.

18. The method recited in claim 12, further comprising compressing the methane molecules prior to illumination.

19. The method recited in claim 12, further comprising compressing the water molecules prior to illumination.

* * * * *